(12) United States Patent
Froschmeier et al.

(10) Patent No.: US 10,301,275 B2
(45) Date of Patent: May 28, 2019

(54) SWEET TASTE MODULATORS (71) Applicant: Altria Client Services LLC, Richmond, VA (US)

(72) Inventors: Andrea Froschmeier, Ingolstadt (DE); Thomas Hofmann, Neufahn (DE); Christian Schuh, Chesterfield, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 15/462,254

(22) Filed: Mar. 17, 2017

(65) Prior Publication Data
US 2018/0265487 A1 Sep. 20, 2018

(51) Int. Cl.
| | |
|---|---|
| C07D 307/46 | (2006.01) |
| A23L 33/10 | (2016.01) |
| A24B 13/00 | (2006.01) |
| A24B 15/16 | (2006.01) |
| A61K 8/49 | (2006.01) |
| A61K 8/60 | (2006.01) |
| A61K 47/22 | (2006.01) |
| A61K 47/26 | (2006.01) |
| A61K 9/00 | (2006.01) |
| A61Q 11/00 | (2006.01) |
| C12G 3/06 | (2006.01) |
| A23L 27/00 | (2016.01) |

(52) U.S. Cl.
CPC ............ *C07D 307/46* (2013.01); *A23L 27/88* (2016.08); *A23L 33/10* (2016.08); *A24B 13/00* (2013.01); *A61K 8/4973* (2013.01); *A61K 8/60* (2013.01); *A61K 9/0053* (2013.01); *A61K 47/22* (2013.01); *A61K 47/26* (2013.01); *A61Q 11/00* (2013.01); *C12G 3/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,080,279 A | 3/1963 | Constantin et al. | |
| 3,095,882 A | 7/1963 | Hind et al. | |
| 4,277,511 A | 7/1981 | Bliznak et al. | |
| 4,803,082 A | 2/1989 | Cherukuri et al. | |
| 4,906,480 A | 3/1990 | Kashket | |
| 5,672,372 A | 9/1997 | Kim et al. | |
| 7,851,000 B2 | 12/2010 | Boghani et al. | |
| 7,851,005 B2 | 12/2010 | Bingley et al. | |
| 8,119,821 B2 | 2/2012 | Shigemura et al. | |
| 8,449,936 B2 | 5/2013 | Daniher et al. | |
| 8,455,033 B2 | 6/2013 | Boghani et al. | |
| 8,609,173 B2 | 12/2013 | Shigemura et al. | |
| 8,679,567 B2 | 3/2014 | Hansen et al. | |
| 8,709,521 B2 | 4/2014 | Prakash et al. | |
| 8,715,761 B2 | 5/2014 | Deniher et al. | |
| 8,754,088 B2 | 6/2014 | Shigemura et al. | |
| 8,765,205 B2 | 7/2014 | Hansen et al. | |
| 9,138,011 B2 | 9/2015 | Putter et al. | |
| 9,642,384 B2 * | 5/2017 | Schuh | A23L 2/56 |
| 2006/0248602 A1 | 11/2006 | Bufe et al. | |
| 2007/0267033 A1 | 11/2007 | Mishra et al. | |
| 2007/0269570 A1 | 11/2007 | Degenhardt et al. | |
| 2008/0178894 A1 | 7/2008 | Zimmermann | |
| 2008/0292765 A1 * | 11/2008 | Prakash | A23L 27/88 426/548 |
| 2009/0069551 A1 | 3/2009 | Hofmann et al. | |
| 2009/0131690 A1 | 5/2009 | Gruter et al. | |
| 2009/0156841 A1 | 6/2009 | Sanborn et al. | |
| 2009/0175995 A1 | 7/2009 | Havekotte et al. | |
| 2010/0040733 A1 | 2/2010 | Blank et al. | |
| 2010/0331349 A1 | 12/2010 | Ley et al. | |

(Continued)

FOREIGN PATENT DOCUMENTS

| | | |
|---|---|---|
| EP | 1252825 A1 | 10/2002 |
| EP | 2119372 A1 | 11/2009 |

(Continued)

OTHER PUBLICATIONS

Sigma-Aldrich, http://www.sigmaaldrich.com/catalog/product/aldrich/774421?lang=en&region=US; "Identifying 2-Formyl-5-ethoxymethylfuran, 5-(Ethoxymethyl)-2-furaldehyde, 5-Ethoxymethylfurfural, and 5-(ethoxymethyl)furan-2-carboxaldehyde as synonyms", printed May 18, 2017, 4 pages. Mascal, Mark "Conversion of Plant Biomass Into New Generation Biofuels and Value-Added Products", Mascal Res. Grp., http://chemgroups.ucdavis.edu/~mascal/pages/biomass.html ("Mascal"), 2009, 3 pages.
J.S. Camara et al., "Changes in Volatile Composition of Madeira Wines During their Oxidative Ageing", J. Analytica Chimica Acta 563, 2005, 10 pages.
J.S. Camara et al., "3-Hydroxy-4,5-dimethyl-2(5H)-furanone Levels in Fortified Madeira Wines: Relationship to Sugar Content", J. Agricultural & Food Chemistry, vol. 52, No. 22, 2004, pp. 6765-6769.

(Continued)

*Primary Examiner* — Michael P Cohen
(74) *Attorney, Agent, or Firm* — Buchanan Ingersoll & Rooney PC (57) ABSTRACT

Sweet taste modulators for enhancing sweetness of an oral consumer product having a sweetener are described. The sweet taste modulators include 5-ethoxymethyl-2-furaldehyde, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, 3,5-dihydroxybenzoic acid, 2,3,4-trihydroxybenzoic acid, 2,4,6-trihydroxybenzoic acid and 3,4,5-trihydroxybenzoic acid, syringic aldehyde, sinapic aldehyde, ester of 5-hydroxymethylfurfural and vanillic acid, 4-hydrozybenzaldehyde, and 5-methoxymethylfurfural. A method of making 5-ethoxymethyl-2-furaldehyde and a method of making an oral consumer product are also described.

5 Claims, 12 Drawing Sheets

(56) References Cited

U.S. PATENT DOCUMENTS

| | | |
|---|---|---|
| 2011/0104351 A1 | 5/2011 | George et al. |
| 2011/0177085 A1 | 7/2011 | Bufe et al. |
| 2011/0212240 A1 | 9/2011 | Zehentbauer et al. |
| 2012/0231140 A1 | 9/2012 | Hofmann et al. |
| 2012/0288605 A1 | 11/2012 | George et al. |
| 2013/0087159 A1 | 4/2013 | Sweeney et al. |
| 2013/0190516 A1 | 7/2013 | Benecke et al. |
| 2014/0261485 A1 | 9/2014 | Kobal et al. |
| 2014/0271873 A1 | 9/2014 | Gogova et al. |
| 2014/0271946 A1 | 9/2014 | Kobal et al. |
| 2015/0257428 A1* | 9/2015 | Schuh ................ A23L 2/56 426/62 |
| 2016/0183576 A1 | 6/2016 | Wonschik et al. |

FOREIGN PATENT DOCUMENTS

| | | |
|---|---|---|
| EP | 2135513 A1 | 12/2009 |
| EP | 2135514 A1 | 12/2009 |
| EP | 2135515 A1 | 12/2009 |
| EP | 2404172 A1 | 1/2012 |
| EP | 2494874 A1 | 9/2012 |
| JP | 2006238814 A | 9/2006 |
| JP | 2006238815 A | 9/2006 |
| JP | 2006238828 A | 9/2006 |
| JP | 2006238829 A | 9/2006 |
| KR | 20140108508 A | 9/2014 |
| PT | 1427703 E | 3/2013 |
| RU | 2007118606 A | 11/2008 |
| WO | 2005096841 A1 | 10/2005 |
| WO | 2006003107 A1 | 1/2006 |
| WO | WO-2008056135 A2 * | 5/2008 ............ A24B 13/00 |
| WO | 2013121264 A1 | 8/2013 |
| WO | 2014151433 A1 | 9/2014 |
| WO | 2014151434 A2 | 9/2014 |

OTHER PUBLICATIONS

Ley et al., "Enhancers for Sweet Taste from the World of Non-Volatiles: Polyphenols as Taste Modifiers," Sweetness and Sweeteners, ACS Symposium Series, [Abstract], 979:400-409 (2008), 1 page.

Servant et al. "Positive allosteric modulators of the human sweet taste receptor enhance sweet taste," Proceedings of the National Academy of Sciences, [Abstract], 107(10), 4746-4751 (2010)), 1 page.

Hillmann et al., "Sensomics analysis of taste compounds in balsamic vinegar and discovery of 5-acetoxymethyl-2-furaldehyde as a novel sweet taste modulator" [Abstract], J. Agric., Food Chem., Oct. 10, 2012, vol. 60, No. 40, 1 page.

* cited by examiner

SWEET TASTE MODULATORS

FIELD OF INVENTION

The disclosure relates to sweet taste modulators useful for enhancing sweetness of an oral consumer product comprising a sweetener.

BACKGROUND

Recent research efforts into food science have been increasingly focused in developing compositions comprising a reduced amount of natural sweetener without compromising the preferred sweet taste. Although naturally-occurring carbohydrate sweeteners, such as sucrose, are the most widely used sweeteners, they suffer from the disadvantages of high cost and high caloric content. Artificial sweeteners have been designed that overcome these problems but they are sometimes rejected by the consumer for not having a sufficiently "sucrose-like" taste. Artificial sweeteners have different sweetness profiles from that of sucrose and often suffer from side effects such as delays in the onset of sweetness perception and/or unpleasant aftertastes.

Figure 1:
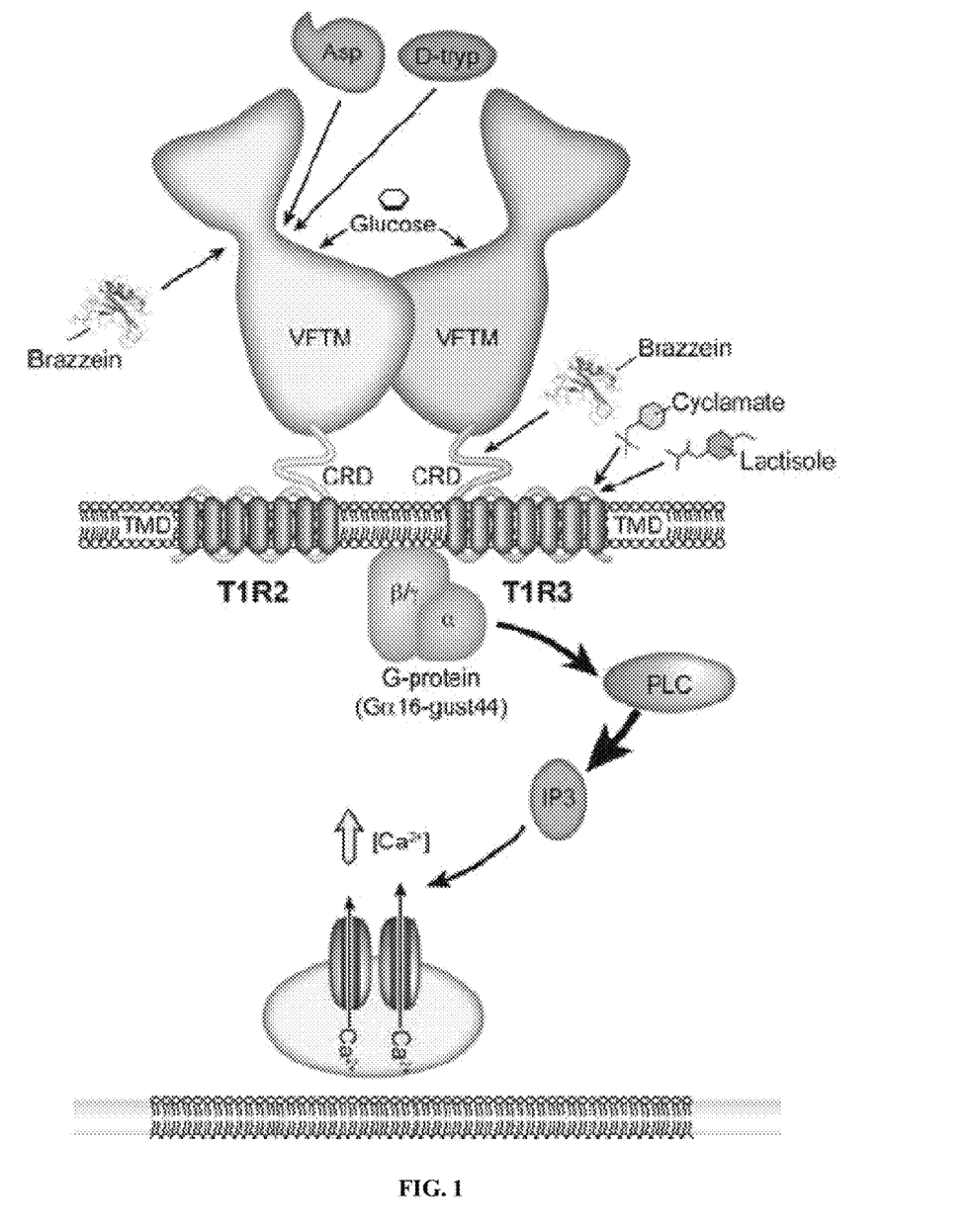
FIG. 1 shows the interactions between a heterodimeric sweet receptor and sweet ligands.

The perception of sweet taste is mediated by T1R2 and T1R3 G-protein coupled receptors. Heterodimers of T1Rs are necessary for the detection of sweet stimuli. FIG. 1 shows the interaction of the heterodimeric sweet receptor and selective sweet ligands, demonstrating the structural diversity of agonists and their different binding sites. Taste modulators do not directly activate taste receptors; they are able to interact with the receptor and influence the binding affinity of direct agonists.

Certain sweet taste enhancers are already described in literature. Ley et al. ("Enhancers for Sweet Taste from the World of Non-Volatiles: Polyphenols as Taste Modifiers," Sweetness and Sweeteners, ACS Symposium Series, 979 (25), 400-409 (2008)) characterized hydroxylated benzoic acid amides. Servant et al. ("Positive allosteric modulators of the human sweet taste receptor enhance sweet taste," Proceedings of the National Academy of Sciences, 107 (10), 4746-4751 (2010)) determined three compounds with sweet enhancing character and suggest that these compounds enables a stabilization of the closed form of the Venus flytrap domain of the T1R2-subunit.

Thus, there is an increasing interest in the food industry in taste modulators due to their ability to improve the sweet taste of products by masking and reducing the perception of undesirable flavors while optimizing and enhancing positive sweetness. Despite progress in developing methods for identifying new taste modulators, there is still a need for oral compositions that include sweetness modulators. Moreover, the high demand for low- or non-caloric, natural and synthetic sweeteners has promoted further development of sweet taste modulators as low-cost, low-caloric alternatives that would reduce the quantity of natural or artificial sweeteners in orally delivered products.

In particular, there is a need for a new sweetness modifier which is capable of increasing the sucrose equivalence of a sweetener. Furthermore, there is a need for a sweetener composition that is capable of increasing the sucrose equivalence, as well as, modifying the perception of sweet flavor of the sweetener, the aftertaste of the sweetener, the sweetness onset period of the sweetener, the sweetness peak period of the sweetener and/or the sweetness decay period of the sweetener. Human sweet taste receptors adapt to the perception of sweet taste over time to decrease: (1) maximum intensity of taste perception experienced, (2) total amount of taste perception experienced and (3) total duration of taste perception experienced. The sweet taste modifiers disclosed herein affect human sweet taste receptors to result in an increased (1) maximum intensity of taste perception experienced, (2) total amount of taste perception experienced and (3) total duration of taste perception experienced.

SUMMARY

An oral consumer product is disclosed comprising at least one sweetener; at least one sweet taste modulator comprising 5-ethoxymethyl-2-furaldehyde, wherein the sweet taste modulator is present in an amount effective to enhance the sweetness of the at least one sweetener.

In one embodiment, the oral consumer product comprises at least one sweetener selected from the group consisting of sucrose, fructose, glucose, and maltose.

In one embodiment, the oral consumer product comprises a sweet taste modulator present in a concentration ranging from about $1 \times 10^{-10}$ wt % to 5 wt %.

In one embodiment, the oral consumer product is a foodstuff, a pharmaceutical, a tobacco product, a personal care product, or a beverage.

In one embodiment, the oral consumer product is a beverage.

In one embodiment, the oral consumer product is an alcoholic beverage.

In one embodiment, the oral consumer product is: (a) a foodstuff comprising at least one of confectioneries; gummies; soft candies; edible films; lozenges; pressed tablets; cereals; cereal bars; chewing gum; frozen or refrigerated/perishable food products; dairy components; puddings; whipped toppings and condiments; jams; jellies; peanut butter; syrups; toppings; fruit or vegetable sauces; baked goods; sweet and salty snacks; and dry or powder mixes; beverages; or (b) a pharmaceutical comprising at least one of an orally-delivered tablet; capsule; solution; oral spray; and linctus; or (c) a tobacco product comprising at least one tobacco-containing moist or dry smokeless tobaccos including snus-style products and snuff products; loose tobacco in a pouch or pack; chewing tobaccos; tobacco lozenge; dissolvable tobacco orb; pellet; strip; tobacco coated dowel; dipping tobacco; chewing tobacco gum; tobacco-derived nicotine products, including e-vapor products and polymer discs; or (d) a personal care product comprising an oral personal care product; or (e) a beverage comprising at least one of beer, spirit, liqueur, wine, or a combination comprising at least one of beer, spirit, liqueur and wine.

In one embodiment, the confectioneries comprise chocolates, hard boilings and sugar-based candies; the frozen or refrigerated/perishable food products comprise frozen desserts, frozen confections, and milk-based compositions; the whipped toppings and condiments comprise ketchup, tabletop sweeteners, mustard, mayonnaise, salsas, chutneys, hummus, marinades, and relish; the fruit or vegetable sauces comprise apple sauce and spaghetti sauce; the baked goods comprise cookies, cakes, and bread; the sweet and salty snacks comprise sweetened roasted nuts, kettle corn, and potato snacks; the dry or powder mixes comprise pudding mix, hot chocolate mix, fruit juice mix, drink mix, and lemonade mix; and the beverages comprise soft or carbonated drinks, juice-based drinks, milk-based drinks, beverages made from brewed components, beverage mixes, beverage concentrates, beverages made from dissolvable powdered components, beverage syrups, frozen beverages, and gel beverages.

In one embodiment, the milk-based compositions comprise yogurts, cream, whole milk, low or reduced fat milk, skim milk, milk solids, condensed milk, frozen baked goods, or a combination thereof, or beverages made from brewed components selected from tea and coffee.

In one embodiment, the oral personal care product comprises toothpaste, mouth spray, and mouth wash.

A method of preparing 5-ethoxymethyl-2-furaldehyde is disclosed comprising: (i) reacting 5-hydroxymethyl-2-furaldehyde with ethanol in the presence of an acidic cation-exchange resin to form a mixture comprising 5-ethoxymethyl-2-furaldehyde, and (ii) extracting 5-ethoxymethyl-2-furaldehyde from the mixture of (i) using an organic solvent, e.g., dimethyl ether.

In one embodiment, the acidic cation-exchange resin contains an acidic sulfonic group. For example, the acidic cation-exchange resin can be selected from the group consisting of AMBERLITE IR-120, AMBERLYST 15, AMBERJET 1200, DOWEX 50WX2, DOWEX 50WX4, DOWEX 50WX8, DOWEX HCR, DOWEX 88, DOWEX 650C, DOWEX MARATHON C, DOWEX MSC-1, AND DUOLITE C-26.

In one embodiment, the reaction of (i) occurs at a pH ranging from about 3 to about 6.

In one embodiment, the ethanol is present in the mixture of (i) at a volume percent ranging from about 10 vol % to about 60 vol %.

In one embodiment, the reaction of (i) occurs at a temperature ranging between about 50° C. to about 100° C.

In one embodiment, the mixture of (i) is stirred for at least 48 hours prior to extracting.

An oral consumer product is disclosed comprising: at least one sweetener; at least one sweet taste modulator comprising 5-ethoxymethyl-2-furaldehyde, 2,3-dihydroxybenzoic acid (2,3-DHB), 2,4-dihydroxybenzoic acid (2,4-DHB), 2,5-dihydroxybenzoic acid (2,5-DHB), 2,6-dihydroxybenzoic acid (2,6-DHB), 3,4-dihydroxybenzoic acid (3,4-DHB), 3,5-dihydroxybenzoic acid (3,5-DHB), 2,3,4-trihydroxybenzoic acid (2,3,4-THB), 2,4,6-trihydroxybenzoic acid (2,4,6-THB) and 3,4,5-trihydroxybenzoic acid (3,4,5-THB), syringic aldehyde (SyA), sinapic aldehyde (SinA), ester of 5-hydroxymethylfurfural and vanillic acid (VanMF), 4-hydrozybenzaldehyde (pHBA), and 5-methoxymethylfurfural, wherein the sweet taste modulator is present in an amount effective to enhance the sweetness of the at least one sweetener.

In one embodiment, the sweet taste modulator is present in a concentration ranging from about $1 \times 10^{-10}$ wt % to 5 wt %.

A method of making an oral consumer product is disclosed, comprising: adding at least one sweet taste modulator to the oral consumer product comprising at least one sweetener; the at least one sweet taste modulator comprising 5-ethoxymethyl-2-furaldehyde, 2,3-dihydroxybenzoic acid (2,3-DHB), 2,4-dihydroxybenzoic acid (2,4-DHB), 2,5-dihydroxybenzoic acid (2,5-DHB), 2,6-dihydroxybenzoic acid (2,6-DHB), 3,4-dihydroxybenzoic acid (3,4-DHB), 3,5-dihydroxybenzoic acid (3,5-DHB), 2,3,4-trihydroxybenzoic acid (2,3,4-THB), 2,4,6-trihydroxybenzoic acid (2,4,6-THB) and 3,4,5-trihydroxybenzoic acid (3,4,5-THB), syringic aldehyde (SyA), sinapic aldehyde (SinA), ester of 5-hydroxymethylfurfural and vanillic acid (VanMF), 4-hydrozybenzaldehyde (pHBA), and 5-methoxymethylfurfural, wherein the at least one sweet taste modulator is present in an amount effective to enhance the sweetness of the at least one sweetener.

DETAILED DESCRIPTION

In the following detailed description, specific embodiments are set forth in order to provide a thorough understanding of the products and methods disclosed herein. However, as will be apparent to those skilled in the art, the present embodiments may be practiced without these specific details or by using alternate elements or processes. In other instances, well-known processes, procedures, and/or components have not been described in detail so as not to unnecessarily obscure aspects of embodiments disclosed herein. As used herein in connection with numerical values the term "about" refers to ±10%.

Disclosed herein is at least one sweet taste modulator, for example, 5-ethoxymethyl-2-furaldehyde (EMF), and a method of forming thereof. The sweet taste modulator can be used to enhance sweetness of an orally-delivered consumer product comprising a sweetener.

Whiskey is a possible source for next-generation sweet taste modulators due to the presence of ethanol and 5-hydroxymethyl-2-furaldehyde (5-HMF), both of which contribute to the spirit's sweet taste and are available in high concentrations. Specifically, particular attention is given to the formation of EMF through the reaction between 5-hydroxymethyl-2-furaldehyde (5-HMF) and ethanol. Currently, no information exists detailing the influence of EMF or other 5-HMF adducts on the sweet taste perception of alcoholic beverages.

Sweet Taste Modulators

Embodiments described herein provide compositions that may include at least one sweetener and at least one sweet taste modulator. The sweet taste modulator may have controlled-release properties. The sweet taste modulator(s) may work synergistically with the sweetener(s) to enhance the perception of the sweetener(s). Delivery of the sweetener in combination with at least one sweet taste modulator may enhance the sweetness perception upon consumption of the composition. In particular, the sweet taste modulator(s) may function synergistically with the sweetener(s) to enhance the sweetness perception. The incorporation of the sweet taste modulator(s), therefore, allows for reduced amounts of sweetener(s) without compromising the level of sweetness provided by the composition. Due to the high calories contained in many conventional sweeteners, such as sugar, these results may be highly desirable. Additionally, there may be significant cost savings associated with the reduction in sweetener amounts used in the composition.

For purposes of some embodiments described herein, a "sweet taste modulator" refers to a substance that enhances the perception of a sweetener during consumption of a composition containing the sweetener. For purposes of some embodiments described herein, the term "enhance" means to intensify, supplement, modify, modulate or potentiate.

The sweet taste modulator may have a synergistic effect when used in conjunction with a sweetener, i.e., by enhancing the taste effects of the sweetener such that the total effect is greater than the sum of the taste effects of the individual substances alone. In addition, some sweet taste modulators do not introduce a characteristic taste and/or aroma perception of their own.

Preferably, the sweet taste modulator is selected from the group consisting of 5-ethoxymethyl-2-furaldehyde (EMF), 2,3-dihydroxybenzoic acid (2,3-DHB), 2,4-dihydroxybenzoic acid (2,4-DHB), 2,5-dihydroxybenzoic acid (2,5-DHB), 2,6-dihydroxybenzoic acid (2,6-DHB), 3,4-dihydroxybenzoic acid (3,4-DHB), 3,5-dihydroxybenzoic acid (3,5-DHB), 2,3,4-trihydroxybenzoic acid (2,3,4-THB), 2,4,6-trihydroxybenzoic acid (2,4,6-THB) and 3,4,5-trihydroxybenzoic acid (3,4,5-THB), syringic aldehyde (SyA), sinapic aldehyde (SinA), ester of 5-hydroxymethylfurfural and vanillic acid (VanMF), 4-hydrozybenzaldehyde (pHBA), 5-methoxymethylfurfural, and combinations thereof. More preferably, the sweet taste modulator is 5-ethoxymethyl-2-furaldehyde, which enhances the sweetness of added sweeteners but does not itself have a taste.

In some embodiments, the concentration of the sweet taste modulator sufficient to enhance the taste of the sweetener is about $1\times10^{-10}$ wt % to 5 wt %, or preferably $1\times10^{-8}$ wt % to 1 wt %, or more preferably $1\times10^{-6}$ wt % to 0.1 wt %, or most preferably $1\times10^{-4}$ wt % to 0.1 wt %, based on the total weight of the composition.

Sweeteners

The sweetener may be a nutritive sweetener or non-nutritive sweetener or a combination thereof.

Non-limiting examples of nutritive sweeteners include: sucrose, liquid sucrose, fructose, liquid fructose, glucose, liquid glucose, glucose-fructose syrup from natural sources such as apple, chicory, agave, honey, etc., e.g., high fructose corn syrup, chicory syrup, agave syrup, invert sugar, medium invert sugar, maple syrup, maple sugar, honey, brown sugar molasses, e.g., cane molasses and sugar beet molasses, sorghum syrup, caramel, dried fruits, cocoa, carob bean extract, liquorice, and mixtures of any of them.

Non-limiting examples of non-nutritive natural sweeteners include: rebaudioside A, rebaudioside D, stevioside, other steviol glycosides, Stevia rebaudiana extracts, Lo Han Guo (LHG), e.g., LHG juice concentrate or LHG powder, monellin, brazzein, monatin, and mixtures of any of them. Other examples of non-nutritive sweeteners include sorbitol, mannitol, xylitol, glycyrrhizin, maltitol, maltose, lactose, xylose, arabinose, isomalt, lactitol, trehalulose, ribose, fructo-oligosaccharides, and mixtures of any of them. The sweetener component may include erythritol, tagatose, an erythritol and tagatose blend, or polydextrose.

Non-limiting examples of non-nutritive artificial sweeteners include: peptide based sweeteners, e.g., aspartame, neotame, and alitame, and non-peptide based sweeteners, e.g., sodium saccharin, calcium saccharin, acesulfame (including but not limited to acesulfame potassium), cyclamate (including but not limited to sodium cyclamate and/or calcium cyclamate), neohesperidin dihydrochalcone, sucralose, and mixtures of any of them.

Oral Consumer Products

In some embodiments, an oral consumer product may comprise at least one sweetener and at least one sweet taste modulator.

The oral consumer product may be a foodstuff, a pharmaceutical, a tobacco product, a personal care product, or a beverage.

Preferred foodstuffs include at least one of confectioneries, gummies, soft candies, edible films, lozenges, pressed tablets, cereals, cereal bars, chewing gum, frozen or refrigerated/perishable food products, dairy components, puddings, whipped toppings and condiments, jams, jellies, peanut butter, syrups, toppings, fruit or vegetable sauces, baked goods, sweet and salty snacks, dry or powder mixes, beverages, and the like.

Exemplary confectionaries include chocolates, hard boilings, sugar-based candies, and the like.

Exemplary frozen or refrigerated/perishable food products include frozen desserts, frozen confections, milk-based compositions, and the like.

Exemplary milk-based compositions include yogurts, cream, whole milk, low or reduced fat milk, skim milk, milk solids, condensed milk, frozen baked goods, a combination thereof, and the like or beverages made from brewed components selected from tea, coffee, and the like.

Exemplary whipped toppings and condiments include ketchup, tabletop sweeteners, mustard, mayonnaise, salsas, chutneys, hummus, marinades, relish, and the like.

Exemplary fruit or vegetable sauces include apple sauce, spaghetti sauce, and the like. Exemplary baked goods include cookies, cakes, bread, and the like.

Exemplary sweet and salty snacks include sweetened roasted nuts, kettle corn, potato snacks, and the like.

Exemplary dry or powder mixes include pudding mix, hot chocolate mix, fruit juice mix, drink mix, lemonade mix, and the like.

Exemplary beverages include soft or carbonated drinks, juice-based drinks, milk-based drinks, beverages made from brewed components, beverage mixes, beverage concentrates, beverages made from dissolvable powdered components, beverage syrups, frozen beverages, gel beverages, and the like.

Preferred pharmaceuticals include at least one of an orally-delivered tablet, capsule, solution, oral spray, linctus, and the like.

Preferred tobacco products include at least one of a tobacco-containing orally-delivered chewing tobacco, snuff, tobacco lozenge, dissolvable tobacco orb, pellet, strip, toothpick-sized stick, dipping tobacco, tobacco gum, snus, and the like.

Preferred personal care products include an oral personal care product and the like. Exemplary oral personal care products include toothpaste, mouth spray, mouth wash, and the like.

Preferred beverages include at least one of beer, spirit, liqueur, wine, a combination comprising at least one of beer, spirit, liqueur and wine, and the like. In some embodiments, the level of alcohol, as measured by the amount of ethanol contained in the beverage composition can be about 0.5 vol % to about 80 vol % based on the total volume of the beverage composition.

Confectionery and solid pharmaceutical delivery forms optionally can be coated.

In some embodiments, the oral consumer product may include a confectionery base or gum base and any of the compositions described herein. In some embodiments, some or all of the sweetener and/or the sweet taste modulator may be employed in a free form (e.g., unencapsulated). Alternatively, the product may include some or all of the sweetener and/or the sweet taste modulator in an encapsulated form. As a further alternative, the product may include some of the sweetener and/or the sweet taste modulator in a free form and some of the sweetener and/or the sweet taste modulator in an encapsulated form.

The following are non-limiting examples of the present invention:

Example 1—Preparation of 5-ethoxymethyl-2-furaldehyde 5-ethoxymethyl-2-furaldehyde was prepared by conversion of 5-HMF in ethanol in the presence of an acidic cation-exchange resin, preferably, an acidic cation-exchange resin having an acidic sulfonic group, and more preferably, a macro reticular polystyrene-based ion-exchange resin with strongly acidic sulfonic group, e.g., AMBERLYST-15, as a catalyst at approximately 75° C. The reaction mixture was stirred for several hours (e.g., approximately 48 hours) and the resultant mixture was purified, e.g., via preparative high-performance liquid chromatography (HPLC). Ethanol adducts were formed during the stirring step. Due to the semi-volatile character of the resultant compounds, the aqueous HPLC-fractions were extracted with a solvent, e.g., diethyl ether.

After removing the solvent, HPLC chromatograms showed a final composition comprising 5-ethoxymethyl-2-furaldehyde (EMF), 5-(ethoxymethyl)furfural diethylacetal (EMFDEA), and 5-(hydroxymethyl)furfural diethylacetal (HMFDEA).

Figure 2:
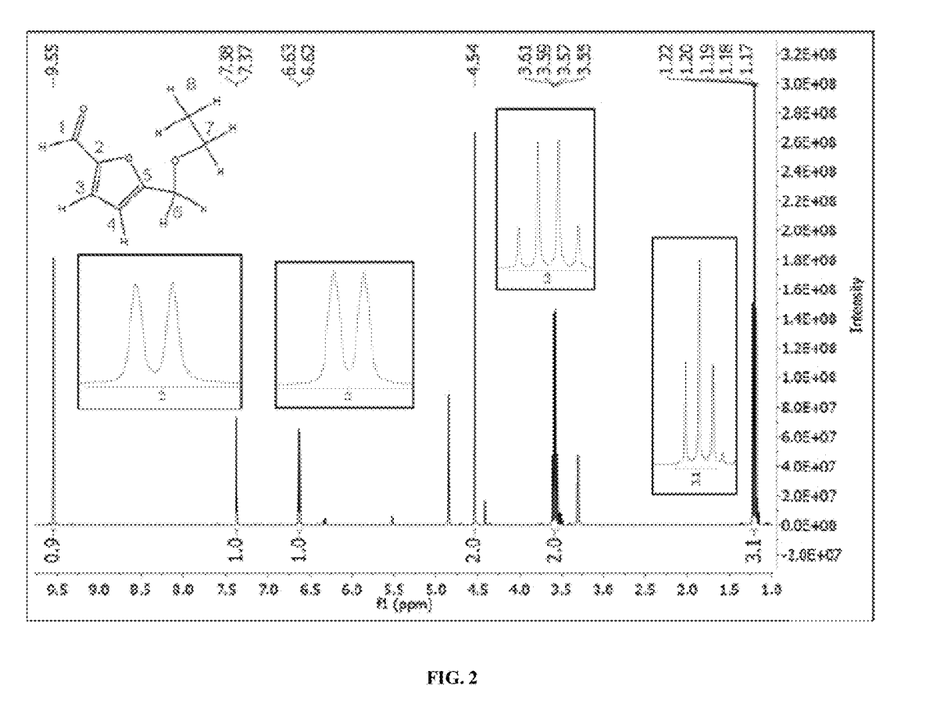
FIG. 2 shows an excerpt of a 1H-NMR spectrum of 5-ethoxymethyl-2-furaldehyde (captured at 400 MHz in methanol-d4) with the chemical structure of 5-ethoxymethyl-2-furaldehyde shown in the top left corner.
Figure 3:
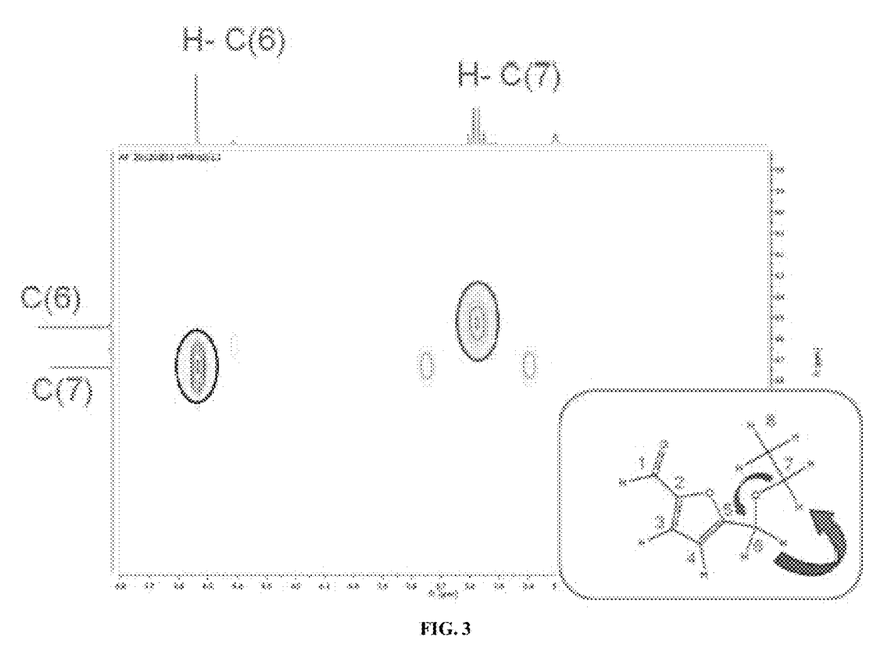
FIG. 3 shows an excerpt of an heteronuclear multiple bond correction (HMBC) spectrum of 5-ethoxymethyl-2-furaldehyde (captured in methanol-d4) with H—C correlation with the chemical structure of 5-ethoxymethyl-2-furaldehyde shown in the bottom right corner.
Figure 4:
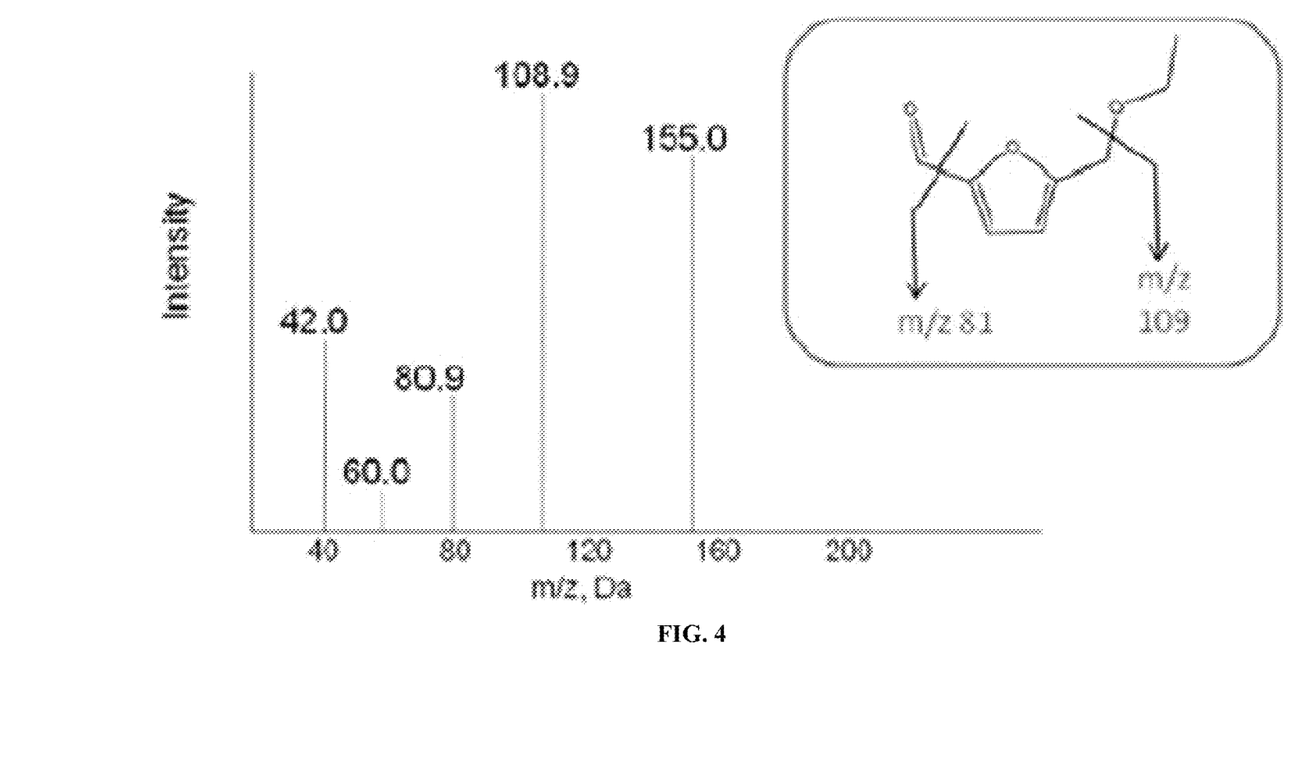
FIG. 4 shows an ESI$^+$ mass spectroscopy fragmentation pattern of 5-ethoxymethyl-2-furaldehyde with the chemical structure of 5-ethoxymethyl-2-furaldehyde shown on the right.

The presence of EMF was verified using Nuclear Magnetic Resonance (NMR) spectroscopy, Heteronuclear Multiple Bond Correlation (HMBC) spectroscopy, and Mass Spectroscopy (MS). Particularly, FIG. 2 shows $^1$H-NMR data of EMF after HPLC processing and confirms the structural integrity of the compound. The four inserts provide blown-up views of the two doublets at 7.38 ppm, 7.37 ppm and 6.63 ppm, 6.62 ppm, respectively, the quadruplet at 3.61 ppm, 3.59 ppm, 3.57 ppm, and 3.55 ppm and the quintuplet at 1.22 ppm, 1.20 ppm, 1.19 ppm, 1.18 ppm, and 1.17 ppm. Moreover, correlations between the H—C(6) protons and the H—C(7) protons and between the C(6) carbon and the C(7) carbon shown in the HMBC spectrum of FIG. 3 confirm that an ethyl moiety was bound at the hydroxyl functional group. The insert shows the overall structure of EMF and locates C(6), C(7), and associated H—C(6) and H—C(7), respectively. Finally, the MS fragmentation pattern of FIG. 4 confirms the molecular structure determined by NMR spectroscopy. The insert represents the overall structure of EMF (having an average mass of approximately 154 Daltons (Da)) along with masses for two characteristic substructures of EMF: $CH(C_4H_2O)CH_2O$ (109 Da) and $(C_4H_2O)CH_2$ (80 Da).

Figure 5:
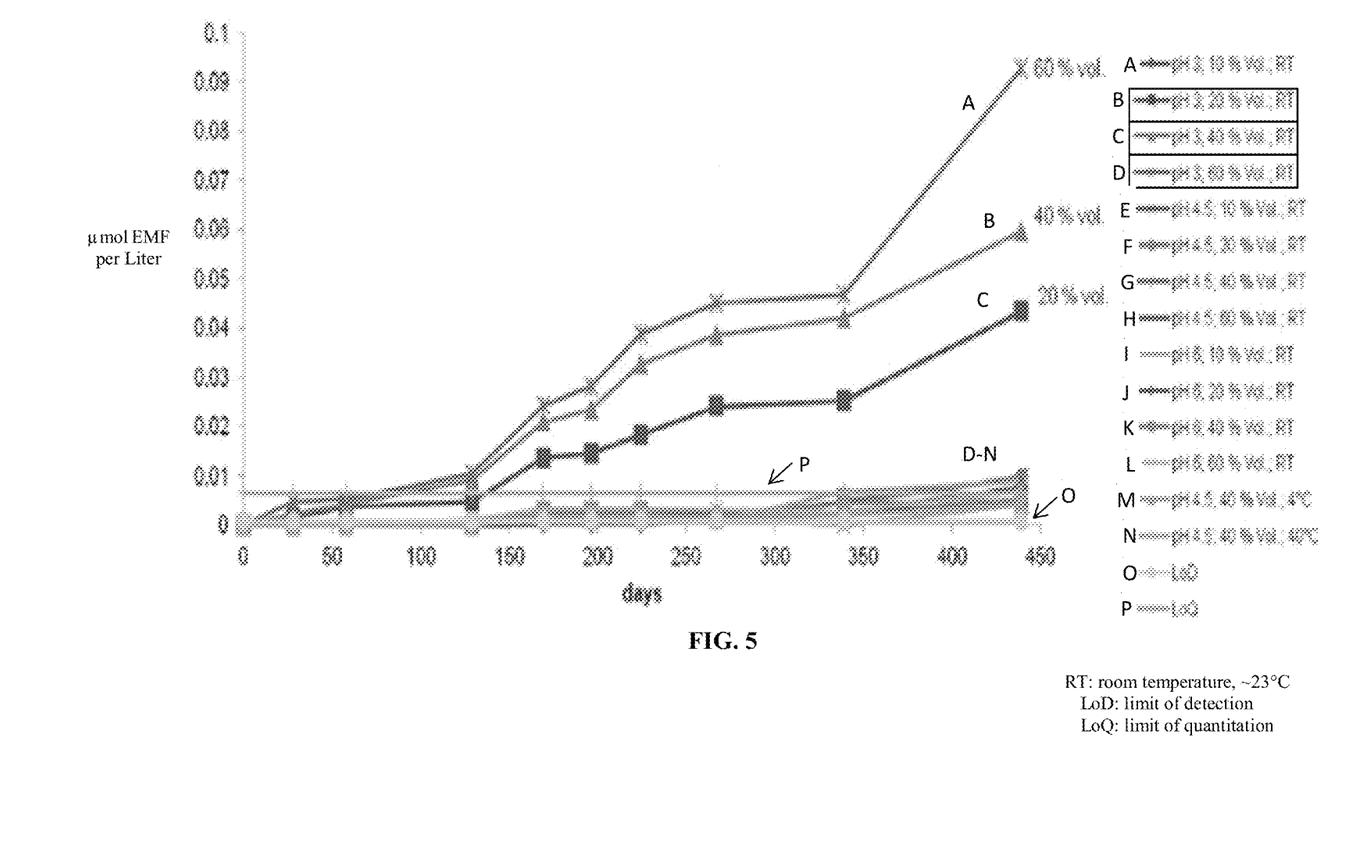
FIG. 5 shows modeling experiments of 5-ethoxymethyl-2-furaldehyde concentrations as a function of time for variable reaction mixture pH and volume percent of ethanol.

The formation of EMF depends on pH, content of ethanol, and temperature used during etherification of 5-HMF with ethanol in the presence of AMBERLYST-15. FIG. 5 depicts modeling experiments illustrating EMF concentrations as a function of mixing time for variable reaction mixture pH, volume percent of ethanol and reaction temperature. Firstly, as shown in FIG. 5, formation of EMF increases with mixing time. Secondly, formation of EMF also depends on pH-value, as the highest concentrations of EMF arise at a pH=3, the lowest and most acidic tested reaction condition. Finally, formation of EMF also increases with ethanol content, as the highest concentrations of EMF arise when ethanol is present at 60 volume percent.

Figure 6:
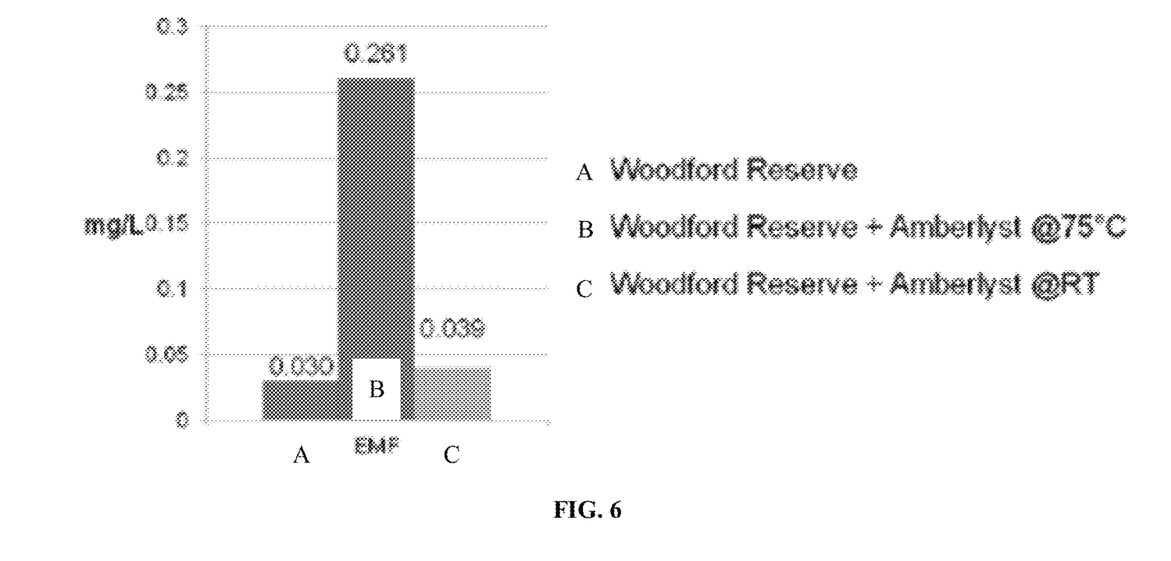
FIG. 6 shows the concentration of 5-ethoxymethyl-2-furaldehyde extracted from Woodford Reserve whiskey.

FIG. 6 illustrates the effects of temperature and catalyst (i.e., AMBERLYST-15) on the concentration of 5-ethoxymethyl-2-furaldehyde (EMF) separated from Woodford Reserve whiskey. Techniques used to separate EMF include, for example, extraction, decantation, chromatography, distillation, elutriation, evaporation, filtration, flocculation, fractionation, and stripping. At 75° C., formation of EMF (0.261 mg/L) (column "B") is more than six times the formation of EMF at room temperature (0.039 mg/L) (column "C"). Moreover, the presence of a strong acidic catalyst (i.e., AMBERLYST-15) also results in a 30 percent increase in EMF yield (0.039 mg/L) than without such strong acidic catalyst (0.030 mg/L) (column "A").

Example 2—Sweet Enhancing Experiments

The influence of the sweet taste modulators on the temporal perception of sweetness can be shown by means of time-intensity tests. For time-intensity tests, a reference solution containing 2 vol % sucrose and 1 vol % ethanol in water and sample solutions (i.e., concentration of stock aqueous solutions listed in Table 1 below) containing 2 vol % sucrose and 1 vol % ethanol and the test compound in different concentrations in water were rated on a horizontal, non-structured line scale from 0 (not detectable) to 10 (very strongly detectable). The reference solution served as a baseline for the time-intensity tests upon which the sample solutions were compared for the temporal perception of sweetness. Twelve panelists were asked to rinse their mouths with an aliquot (10 mL) of a solution and immediately start rating solution's sweet taste intensity for a period of 5 seconds. After 5 seconds, the panelists were instructed to swallow the solution and go on with rating until they did not recognize any sweet taste anymore. The rating results were the averages from the twelve panelists.

TABLE 1

Concentrations of stock solutions for time-intensity tests in ethanol

| Compound | Sample weigt [mg] | Sample volume [mL] | Concentration [mmol] |
|---|---|---|---|
| EMF | 15.4 | 20 | 5 |
| VanMF | 2.8 | 2 | 5 |
| 4-Hydroxybenzaldehyde (pHBA) | 12.2 | 20 | 5 |
| Syringic aldehyde (SyA) | 18.2 | 20 | 5 |
| Sinapic aldehyde (SinA) | 20.8 | 20 | 5 |

Figure 7A:
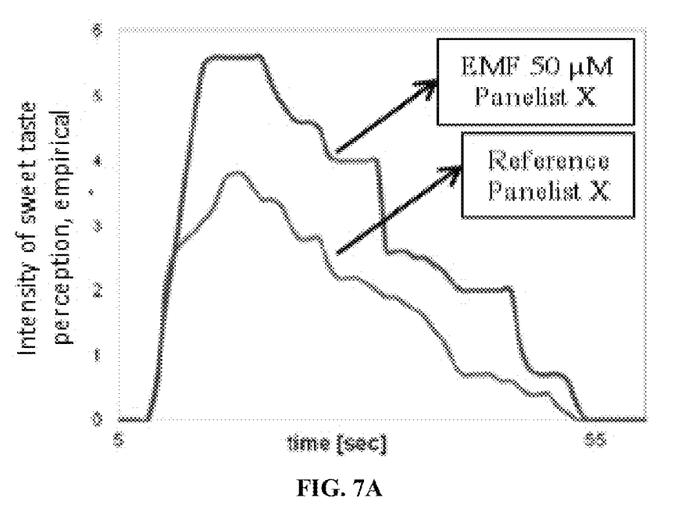
FIGS. 7A and 7B show time-intensity experiments using a reference solution (2% sucrose, 1% ethanol) and 5-ethoxymethyl-2-furaldehyde (50 μM in 2% sucrose, 1% ethanol).
Figure 7B:
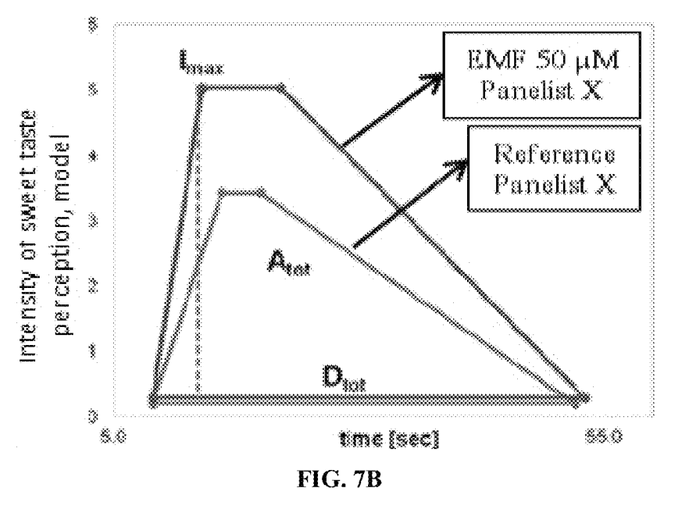

FIGS. 7A and 7B illustrate empirical (FIG. 7A) and predictive (FIG. 7B) model time-intensity experiments using the reference solution containing 2 vol % sucrose and 1 vol % ethanol in water and a sample solution containing 50 μM EMF, 2 vol % sucrose and 1 vol % ethanol in water. Time intensity tests enable continuous measurement of the intensity of taste impressions. For example, FIGS. 7A and 7B show that the sample solution containing 50 μM EMF sustains an elevated maximum intensity ($I_{max}$) of sweet taste perception (approximately '5' on the intensity scale) as compared with the reference solution without any EMF, which has an $I_{max}$ of about 3.5 on the intensity scale. Moreover, this sample solution also delivered a higher total amount of sweet taste perception since the total area under the curve ($A_{total}$) for the sample solution is greater than $A_{total}$ for the reference solution.

After calculating average time intensity (TI) curves using FIZZ biosystems calculations software and determining the TI curves integrated value (i.e., area under the curve), duration, and duration of the increasing and decreasing phase from individual TI curves, the trapezoidal method was applied after extraction of data points at 5% and 95% of the respective maximum intensity on the increasing and decreasing sections of the individual TI curves. The following parameters were extracted for further data analysis: maximum intensity ($I_{max}$) of taste perception experienced, total area under the curve ($A_{total}$) 1 (i.e., total amount) of taste perception experienced and total duration ($D_{total}$) of taste perception experienced. Extracted parameters of sample solutions were normalized on the reference solution from the same evaluation session and a two-way analysis of variance (ANOVA) was conducted.

Table 2 below illustrates an overview of all p-values generated by two-way ANOVA of maximum intensity ($I_{max}$), total area under the curve ($A_{total}$) land total duration ($D_{total}$) for sample solutions containing 5-ethyoxymethylfurfural (EMF), as well as ester of 5-hydroxymethylfurfural and vanillic acid (VanMF), 4-hydrozybenzaldehyde (pHBA), syringic aldehyde (SyA), and sinapic aldehyde (SinA), respectively. P-values (i.e., calculated probabilities) are statistical measures ranging from 0 to 1 which quantify the statistical significance of a data set. In other words, the p-value is a function of the observed sample results (a test statistic) relative to a statistical model, which measures how extreme the observation is. Smaller p-values are indicative of scaling significance. For example, p<0.05 are "significant" (*) (i.e., less than 1 in 20 chance, or 5%, of the data set being erroneous or inaccurate); p<0.01 are "highly significant" () (i.e., less than 1 in 100 chance, or 1%, of the data set being erroneous or inaccurate); and, p<0.001 are "very highly significant" (*) (less than 1 in 1000 chance, or 0.1%, of the data set being erroneous or inaccurate). Measured concentrations of EMF, VanMF, pHBA, SyA, and SinA in the sample solutions used in the statistical analysis are 10 μmol/L, 25 μmol/L, and 50 μmol/L, respectively. The p-values in Table 2 below relate to the statistical significance of the $I_{max}$, $A_{total}$, and $D_{total}$ values of sample solutions containing EMF, VanMF, pHBA, SyA, and SinA, respectively, in FIGS. 8-12.

TABLE 2

Overview of p-values of $I_{max}$, $A_{total}$, and $D_{total}$

| Parameter | | | Concentration [μmol/L] | | |
|---|---|---|---|---|---|
| | | | 10 | 25 | 50 |
| $I_{max}$ | p-value | EMF | 0.1 | <0.001 | <0.001 |
| | | VanMF | <0.01 | <0.01 | 0.2 |
| | | pHBA | 0.9 | <0.001 | <0.01 |
| | | SyA | 0.1 | <0.01 | <0.01 |
| | | SinA | <0.001 | <0.01 | <0.05 |
| $A_{total}$ | p-value | EMF | 0.3 | 0.2 | <0.001 |
| | | VanMF | <0.01 | <0.05 | 0.2 |
| | | pHBA | 0.4 | <0.01 | <0.01 |
| | | SyA | 0.1 | <0.001 | <0.01 |
| | | SinA | <0.05 | <0.01 | <0.01 |
| $D_{total}$[sec] | p-value | EMF | <0.05 | 0.4 | <0.001 |
| | | VanMF | <0.01 | <0.05 | <0.05 |
| | | pHBA | 0.3 | 0.2 | <0.01 |
| | | SyA | 0.5 | <0.05 | 0.3 |
| | | SinA | 0.1 | <0.01 | <0.01 |

Figure 8A:
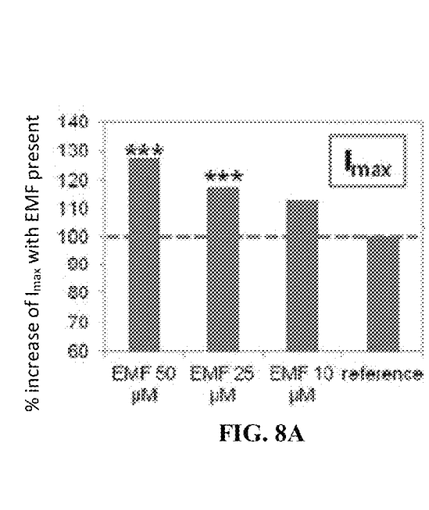
FIGS. 8A, 8B, and 8C show $I_{max}$, $A_{total}$, and $D_{total}$, respectively, of a reference solution (2% sucrose, 1% ethanol) and 5-ethoxymethyl-2-furaldehyde (EMF) present in the reference solution at concentrations of 10 μmol/L, 25 μmol/L, and 50 μmol/L, respectively.
Figure 8B:
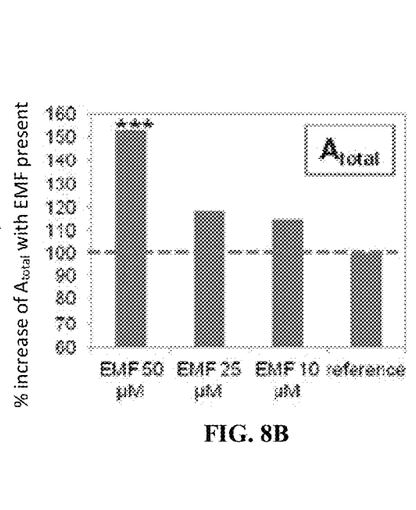
Figure 8C:
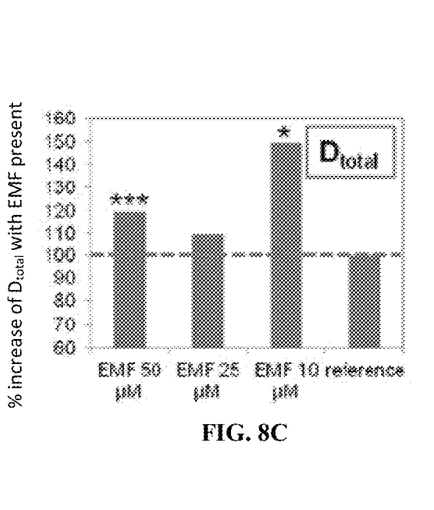

Results shown in FIGS. 8A, 8B, and 8C demonstrate very highly significant (***) increases of $I_{max}$, $A_{total}$ and $D_{total}$ when EMF is present at levels of 50 μM, whereas the presence of 25 μM EMF merely shows a very highly significant increase of the maximum sweet intensity ($I_{max}$), but no significant increases of the total area ($A_{total}$) land the total duration ($D_{total}$). EMF present at 10 μM shows no significant increases in $I_{max}$, $A_{total}$ or $D_{total}$. These findings suggest that EMF is able to increase particularly the perceived intensity and the duration of sweet taste perception at a concentration of at least 50 μM ($7.7 \times 10^{-4}$ wt %).

Figure 9A:
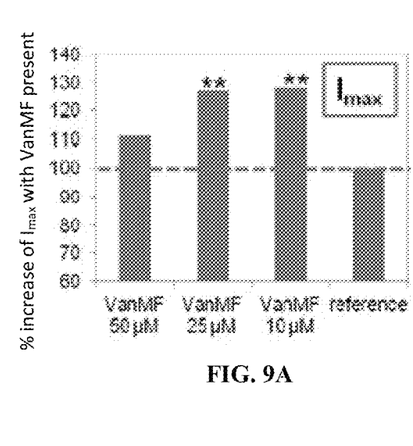
FIGS. 9A, 9B, and 9C show $I_{max}$, $A_{total}$, and $D_{total}$, respectively, of a reference solution (2% sucrose, 1% ethanol) and the ester of 5-hydroxymethylfurfural and vanillic acid (VanMF) present in the reference solution at concentrations of 10 μmol/L, 25 μmol/L, and 50 μmol/L, respectively.
Figure 9B:
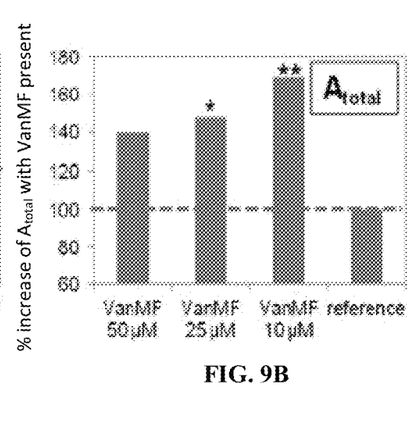
Figure 9C:
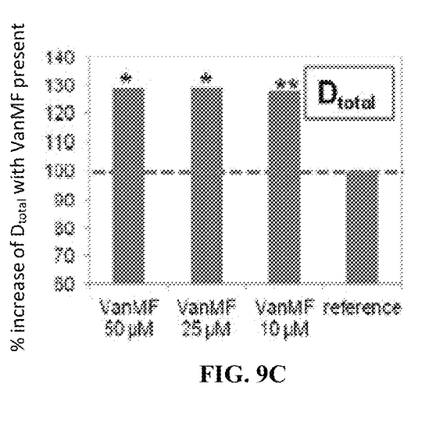

Results shown in FIGS. 9A, 9B, and 9C demonstrate highly significant (**) increases of $I_{max}$, $A_{total}$ and $D_{total}$ when VanMF is present at 10 μM ($2.76 \times 10^{-4}$ wt %), whereas the presence of 50 μM VanMF merely shows a significant (*) increase of the total duration ($D_{total}$) of sweet perception, but no significant increases of the total area ($A_{total}$) land maximum intensity ($I_{max}$). VanMF present at 25 μM shows highly significant (**) increases of maximum sweet intensity ($I_{max}$) and significant (*) increases of the total duration ($D_{total}$) and total area ($A_{total}$). These findings suggest that VanMF is able to increase particularly the perceived intensity and the duration of sweet taste perception; however, different from the sweet taste perception of EMF, VanMF shows its modulating character only at lower concentrations.

Figure 10A:
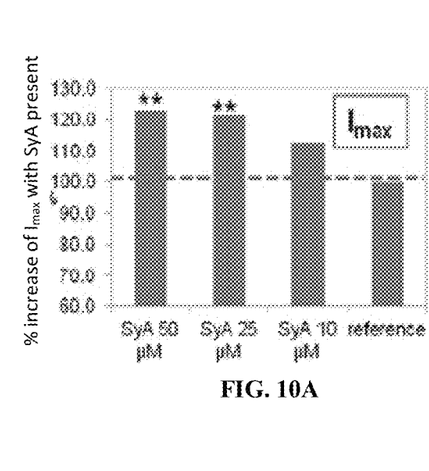
FIGS. 10A, 10B, and 10C show $I_{max}$, $A_{total}$, and $D_{total}$, respectively, of a reference solution (2% sucrose, 1% ethanol) and syringic aldehyde (SyA) present in the reference solution at concentrations of 10 μmol/L, 25 μmol/L, and 50 μmol/L, respectively.
Figure 10B:
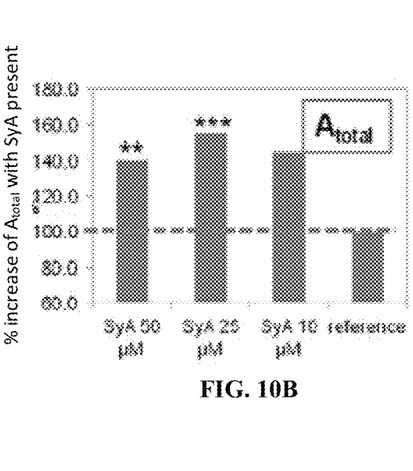
Figure 10C:
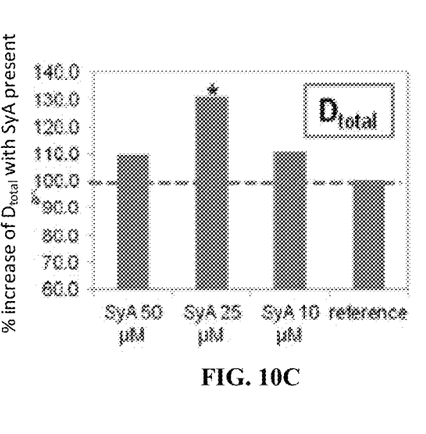

Results shown in FIGS. 10A, 10B, and 10C demonstrate significant increases of $I_{max}$ (), $A_{total}$ (*) and $D_{total}$ (*) when SyA is present at 25 μM ($4.55 \times 10^{-4}$ wt %). Whereas lower concentrations (i.e. 10 μM) do not have a significant influence on sweet perception, higher concentrations (i.e. 50 μM) experience highly significant (**) increases in the maximum intensity ($I_{max}$) and total area ($A_{total}$), but not the total duration ($D_{total}$). Thus, SyA shows the ability to increase particularly the perceived intensity and the duration of sweet taste perception.

Figure 11A:
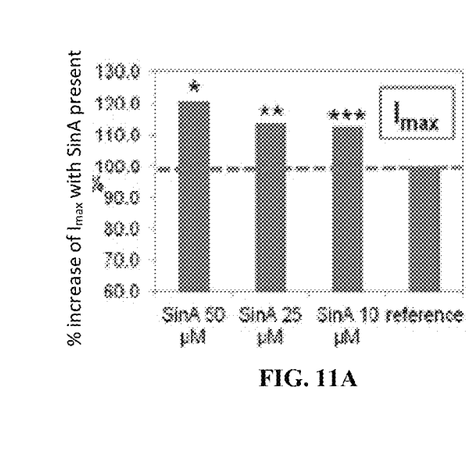
FIGS. 11A, 11B, and 11C show $I_{max}$, $A_{total}$, and $D_{total}$, respectively, of a reference solution (2% sucrose, 1% ethanol) and sinapic aldehyde (SinA) present in the reference solution at concentrations of 10 μmol/L, 25 μmol/L, and 50 μmol/L, respectively.
Figure 11B:
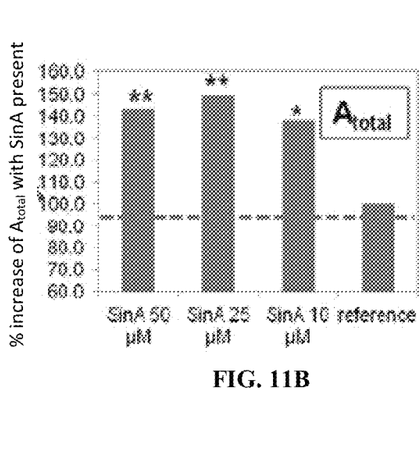
Figure 11C:
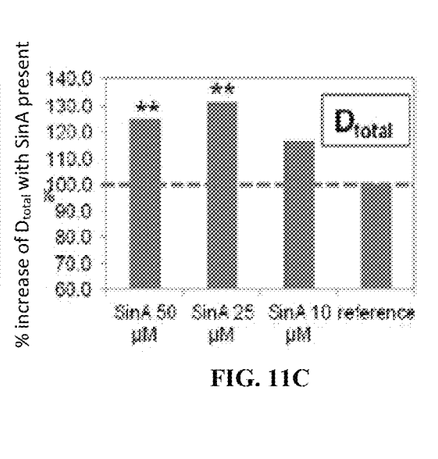

Results shown in FIGS. 11A, 11B, and 11C demonstrate significant increases of $I_{max}$, $A_{total}$ and $D_{total}$ when SinA is present at levels of 50 μM and 25 μM. At 10 μM ($2.08 \times 10^{-4}$ wt %), SinA merely shows significant increases of the total area ($A_{total}$) land the maximum intensity ($I_{max}$) of sweet taste perception, but no significant increase of the total duration ($D_{total}$). Therefore, SinA shows the ability to increase particularly the perceived intensity and the duration of sweet taste perception.

Figure 12A:
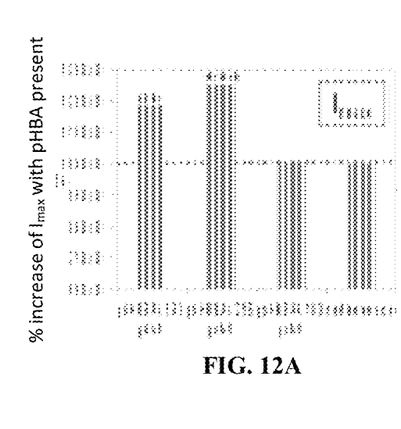
FIGS. 12A, 12B, and 12C show $I_{max}$, $A_{total}$, and $D_{total}$, respectively, of a reference solution (2% sucrose, 1% ethanol) and 4-hydrozybenzaldehyde (pHBA) present in the reference solution at concentrations of 10 μmol/L, 25 μmol/L, and 50 μmol/L, respectively.
Figure 12B:
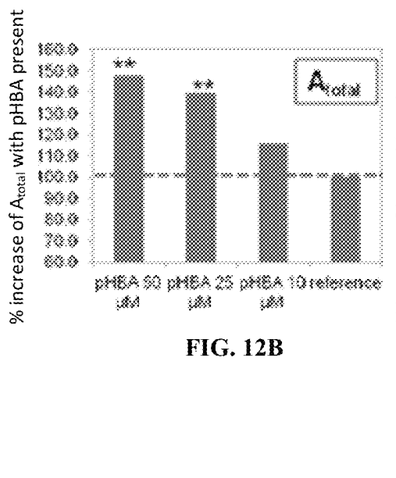
Figure 12C:
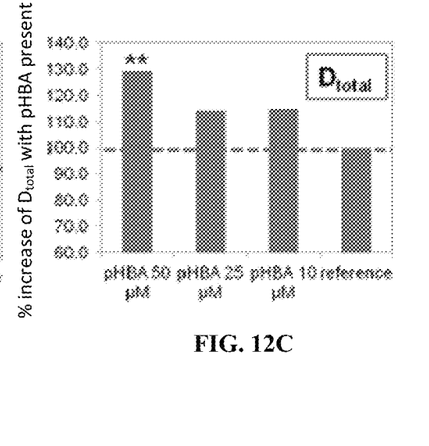

Results shown in FIGS. 12A, 12B, and 12C demonstrate highly significant () increases of $I_{max}$, $A_{total}$ and $D_{total}$ when pHBA is present at levels of 50 μM. At 25 μM, a very highly significant (*) increase of $I_{max}$ is demonstrated and a highly significant (**) increase of $A_{total}$. No significant increases of $I_{max}$, $A_{total}$ or $D_{total}$ are demonstrated when pHBA is present at 10 μM. Therefore, pHBA shows the ability to increase the perceived intensity, total area and duration of sweet taste perception at a concentration of 50 μM ($6.1 \times 10^{-4}$ wt %).

Having described in detail, those skilled in the art will appreciate that, given the disclosure herein, modification may be made to the invention without departing from the spirit of the invention concept. It is not intended that the scope of the invention be limited to the specific and preferred embodiments illustrated and described. All documents referenced herein are hereby incorporated by reference, with the understanding that where there is any discrepancy between this specification and the incorporated document, this specification controls.

We claim:

1. An oral tobacco product comprising:
   at least one sweetener;
   at least one sweet taste modulator comprising 5-ethoxymethyl-2-furaldehyde,
   wherein a ratio of the at least one sweet taste modulator to the at least one sweetener is 7.7-38.5:100 by weight.

2. The oral tobacco product of claim 1, wherein the at least one sweetener is selected from the group consisting of fructose, and glucose.

3. The oral tobacco product of claim 1, wherein the sweet taste modulator is present in a concentration ranging from about $1 \times 10^{-6}$ wt % to 5 wt %.

4. The oral tobacco product of claim 1, wherein the oral tobacco product comprises moist smokeless tobacco or dry smokeless tobacco.

5. The oral tobacco product of claim 1, wherein the oral tobacco product comprises a snus product, a snuff product, a pouch product, chewing tobacco, a tobacco lozenge, a dissolvable tobacco orb, a pellet, a strip, a tobacco-coated dowel, dipping tobacco, chewing tobacco gum, a polymer disc, a sub-combination thereof or a combination thereof.

* * * * *